United States Patent [19]

Lepper

[11] Patent Number: 4,641,658
[45] Date of Patent: Feb. 10, 1987

[54] CARDIAC FLOW MONITOR

[75] Inventor: James M. Lepper, Riverside, Calif.

[73] Assignee: American Hospital Supply Corp., Evanston, Ill.

[21] Appl. No.: 656,515

[22] Filed: Oct. 1, 1984

[51] Int. Cl.⁴ ............................................. A61B 5/02
[52] U.S. Cl. ................................... 128/633; 128/634; 128/664; 128/689; 128/692; 356/39
[58] Field of Search ............... 128/633, 634, 637, 664, 128/666, 668, 689, 692; 356/39

[56] References Cited

U.S. PATENT DOCUMENTS

| | | | |
|---|---|---|---|
| 3,646,931 | 3/1972 | Phelps et al. | 128/689 |
| 3,704,706 | 12/1972 | Herczfeld et al. | 128/633 |
| 3,998,550 | 12/1976 | Konishi et al. | 356/41 |
| 4,167,331 | 9/1979 | Nielsen | 356/39 |
| 4,201,222 | 5/1980 | Haase | 128/634 |
| 4,306,567 | 12/1981 | Krasner | 128/689 |
| 4,407,290 | 10/1983 | Wilber | 128/633 |
| 4,509,522 | 4/1985 | Manuccia et al. | 128/634 |

Primary Examiner—Kyle L. Howell
Assistant Examiner—Ruth S. Smith
Attorney, Agent, or Firm—Weissenberger and Peterson

[57] ABSTRACT

Previously undesired artifacts in a color signal used in fiberoptic cardiac catheters to measure blood oxygenation levels are used to produce indications of blood flow and true pulse. For this purpose, the color signal is band-pass filtered to derive a DC mean signal level $\mu$ and an AC signal containing only those frequencies at which the signal is affected by blood flow variations. The RMS value of that band-pass-filtered AC signal (which corresponds to the standard deviation $\sigma$ of the AC signal) is divided by the DC value $\mu$ to produce a $\sigma/\mu$ signal representative of flood flow. By clipping the AC signal and using the resulting square wave to drive a one-shot multivibrator, an indication of the patient's true pulse can be obtained.

15 Claims, 7 Drawing Figures

CARDIAC FLOW MONITOR

This invention relates to cardiac flow monitors, and particularly to a method deriving flow and pulse signals from a single color signal in a fiberoptic cardiac catheter.

BACKGROUND OF THE INVENTION

Fiberoptic cardiac catheters are well known in devices which measure the oxygenation of the blood between the heart and the lungs. Typically, a fiber-optic catheter injects into the blood stream light beams of two distinct wavelengths, one of which lies in the red color band and the other in the infrared color band. These signals are reflected and refracted by blood cells, and separate R and IR signals are obtained at the output of the catheter. Because the amplitude of both the R signal and the IR signal is affected, among other things, by artifacts such as clots or flow patterns, the oxygenation of the blood has traditionally been measured by generating an R/IR signal in which the artifacts cancel out. Oxygenation percentage is a known function of the R/IR ratio, and the oxygenation percentage can thus be measured.

One of the parameters which needs to be monitored is the presence or absence (and, to a lesser degree, the amount) of blood flow which is a medically important indication of the heart action and also an indication of whether or not the catheter field of view being examined is blocked by clots or if the catheter is mispositioned. In the prior art, various methods have been used to determine the flow rate. All of these methods required the use of apparatus other than the fiberoptic catheter itself. Also, the heart action was generally monitored by means of an EKG. The EKG, however, indicates only electric impulses to the heart muscle and does not reflect the actual pumping action of the heart muscle which, in a sick patient, is not necessarily the same.

SUMMARY OF THE INVENTION

The invention uses the previously undesired artifacts sensed by a single color sensor of the fiberoptic catheter to derive a flow indication and a true pulse indication by filtering one of the color signals (preferably the IR signal) and processing it to obtain a flow representing $\sigma/\mu$ in which $\mu$ is the mean DC signal value and $\sigma$ is the standard deviation of the actual signal from that mean.

More specifically, in the preferred embodiment, the color signal is band-pass filtered to obtain an AC signal containing only those frequency components (in about the 0.6 Hz to 6 Hz range) which represent blood flow artifacts. Artifacts due to electrical interference, turbulence, or breathing are thus eliminated. The root-mean-square (RMS) value of the resulting AC signal is the best first order representation of the flow artifact.

By dividing the true RMS value (which corresponds to the standard deviation $\sigma$ of the AC signal) by the DC value $\mu$, a $\sigma/\mu$ signal is obtained which is a function of the blood flow across the distal end of the fiberoptic catheter. This signal can be displayed on a cardiac flow monitor, or it can be integrated over a minute or so to produce an occlusion signal. When the occlusion signal drops to zero, the medical personnel is advised that blood flow across the catheter tip is blocked by a blood clot or a misalignment of the catheter.

An adjunct of the foregoing process is the ability to measure the patient's real pulse. Unlike the conventional EKG, which detects the electrical impulses which drive the heart, the AC signal of this invention is a function of the actual pumping action of the heart. It can thus be used to detect inconsistencies between the cardiac impulses and the actual heart action, and it can be integrated or averaged over a minute or so to provide a measurement of the patient's true pulse.

It is therefore the object of the invention to use the flow-generated artifacts in a color signal of a fiberoptic cardiac catheter to produce an indication of a blood flow.

It is another object of the invention to use these flow-generated artifacts to produce indications of true pulse and true pulse rate.

DESCRIPTION OF THE PREFERRED EMBODIMENT

Figure 1:
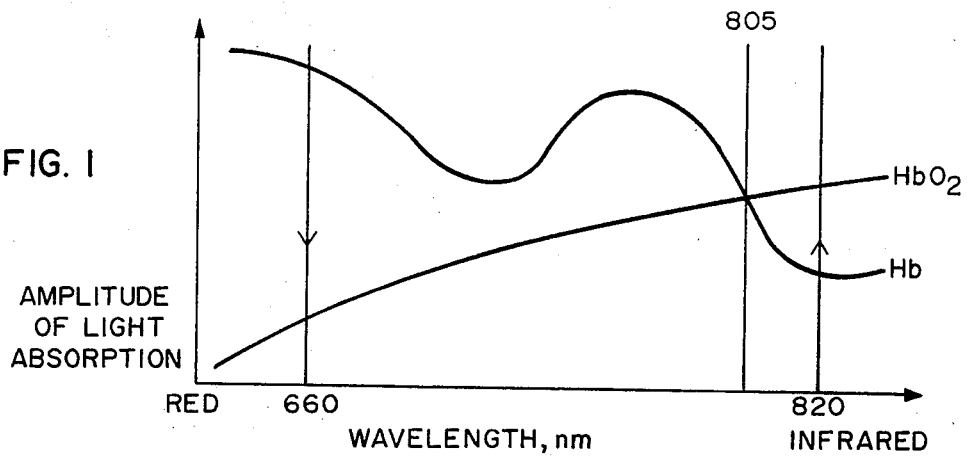
FIG. 1 is a wavelength-amplitude diagram showing the color spectra of hemoglobin and of oxygenated hemoglobin.

FIG. 1 shows the color spectra of hemoglobin (Hb) and oxygenated hemoglobin (HbO$_2$). It will be noted that in general terms, the hemoglobin absorption alone tends to be stronger in the red wavelengths while the oxygenated hemoglobin is stronger in the infrared range. Typical fiberoptic cardiac catheters use standard light-emitting diodes to inject red light at 660 nm and infrared light at approximately 820 nm into the blood stream. This light is reflected and refracted by the blood cells, and the two wavelengths are separately detected at the output of the catheter.

Because blood cells in laminar flow tend to align themselves with one another, artifacts appear in both the red and infrared signals as the blood cells move. Therefore, in order to produce an output in which these artifacts are cancelled out, measurements of blood oxygenation (SV O$_2$) have traditionally used an R/IR signal from which the artifacts are inherently eliminated.

Figure 2:
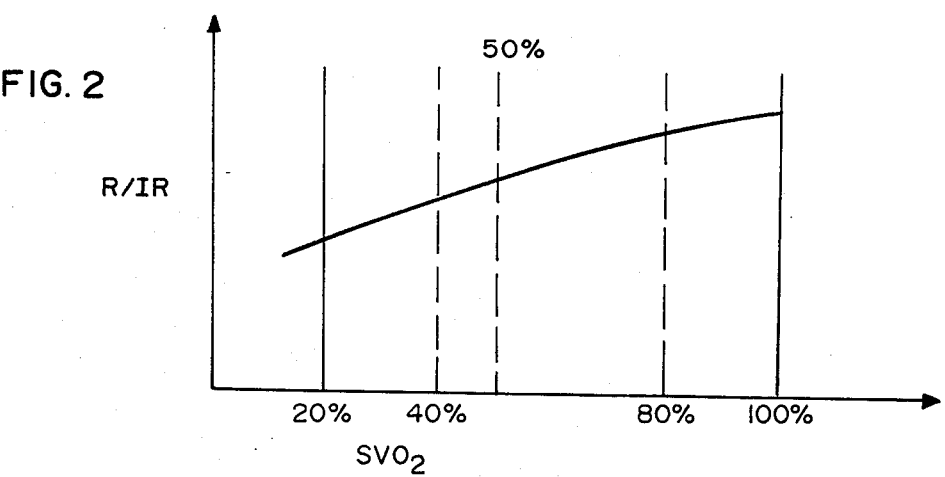
FIG. 2 is a blood saturation-R/IR ratio diagram showing the correspondence between the R/IR ratio and various oxygen saturation percentages of blood.

FIG. 2 shows a typical relation between the R/IR signal and the actual oxygenation percentage of the blood. In the diagram of FIG. 2, 80% represents normal blood oxygenation, 50% indicates sickness, and 40% indicates the need for immediate medical intervention.

Because static blood cells array themselves to an adjacent surface such as the fiberoptic window, while flowing cells array themselves parallel to shear in the boundary layer, the light reflection is decreased in static cells and increased in flowing cells. Consequently, the alternation between static and flowing conditions immediately following the heart valve in the course of a pulse created artifacts which were previously considered undesirable. These artifacts varied the light intensity by about 50% in the course of a pulse.

Figure 3:
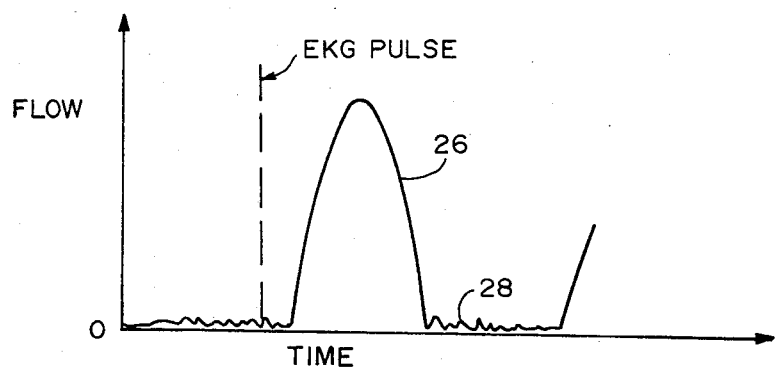
FIG. 3 is a time-amplitude diagram illustrating actual blood flow during a single heartbeat cycle.
Figure 4:
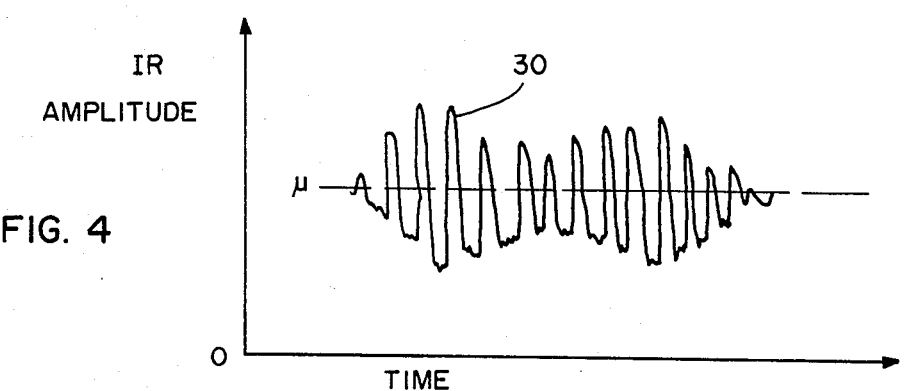
FIG. 4 is a time-amplitude diagram illustrating the variations in the color signal as a function of time, covering many heartbeats and two respiration cycles.

Referring now to FIG. 3, it will be seen that the blood flow fluctuates along the general lines of FIG. 3 when blood alternately flows and stops as a result of the heart's pumping action. The dominant portion of the signal artifact shown in FIG. 3 is the pressure pulse 26 during which the blood flows through the artery, and which is followed by a low level of noise while the blood is essentially stagnant between heartbeats.

If the amplitude of the infrared signal, for example, is plotted as a function of time, a trace will be obtained in which the signal 30 has a mean DC value of $\mu$ and in which an AC component is superimposed upon the DC value $\mu$. It has been found that if the RMS value of that AC component (preferably within a limited frequency range) is divided by the DC value $\mu$, an indication of blood flow can be obtained. The DC component $\mu$ depends on the catheter properties and the average blood properties such as hematocrit and concentration of various light scatterers in the blood plasma. Thus we divide by $\mu$ to scale the signal. The RMS value of the AC component is, in effect, the standard deviation $\sigma$ of the IR signal curve.

Figure 5:
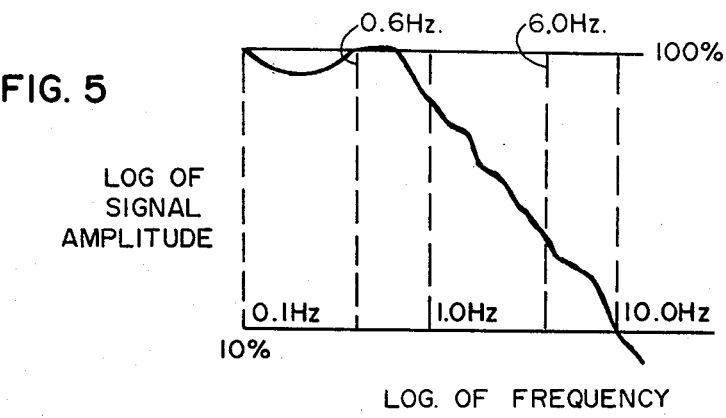
FIG. 5 is a log-log frequency-amplitude diagram illustrating the amplitude of the color signal at various frequencies.

If, as in FIG. 5, the signal amplitude is logarithmically plotted against the frequency components of the signal, it will be noted that most of the signal lies in the range between 0.1 Hz and 1.0 Hz, and then falls off rapidly as it gets toward 10 Hz. Consequently, the ideal frequency range for which the RMS value of the AC component should be determined lies in the range of about 0.6 Hz and 6 Hz. Below 0.6 Hz the signal tends to be affected by the patient's breathing, and above 6 Hz, the relative amplitude of the signal drops off too much to be useful. Also, frequencies substantially above 10 Hz need to be suppressed to eliminate interference from the commercial AC power supply.

Figure 6:
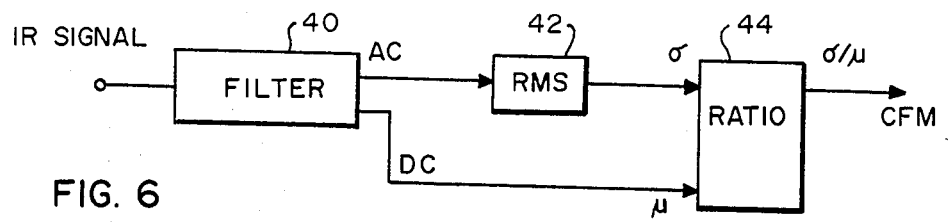
FIG. 6 is an overall diagram of the circuit of this invention.
Figure 7:
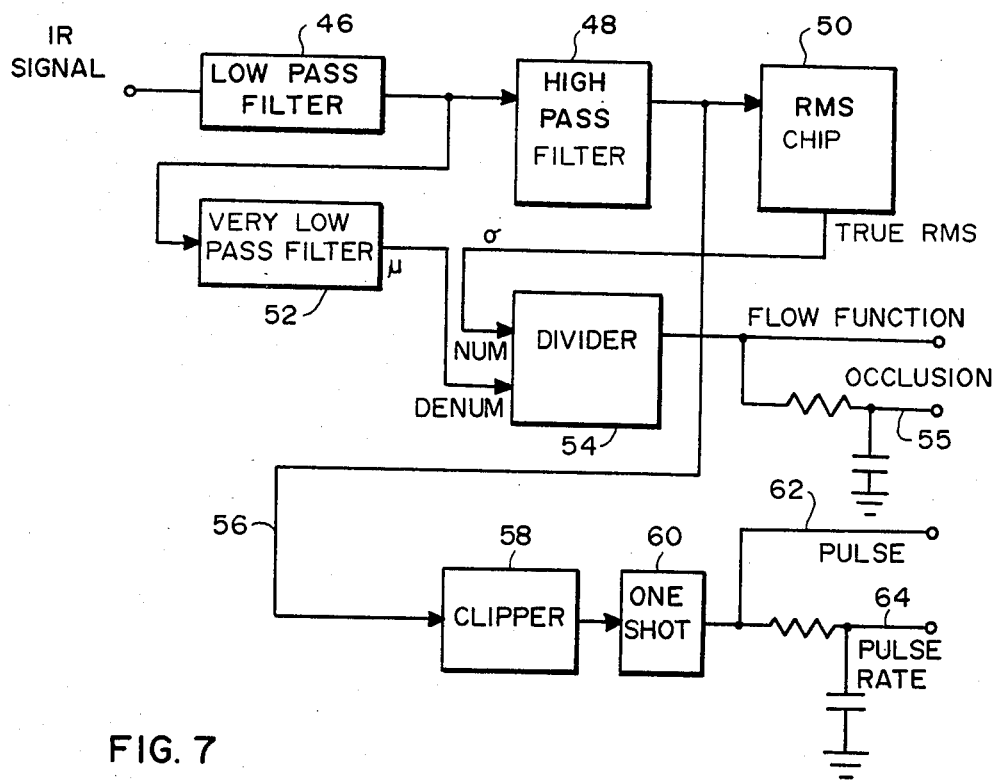
FIG. 7 is a more detailed version of the block diagram of FIG. 6.

With these considerations in mind, FIG. 6 and 7 show the processing of the IR signal to obtain flow and pulse indications. As shown in FIG. 6, the IR signal is basically filtered by filter 40 to produce AC and DC outputs. The RMS of the AC output is then determined by an RMS circuit 42. Either or both 40 and 42 may be analog or digital. The output of the RMS circuit 42 is the standard deviation $\sigma$, while the DC output represents the mean value $\mu$. These two values are then divided by each other in a ratio or divider circuit 44 to produce an output of $\sigma/\mu$ which is an indication of the blood flow. As a simple occlusion monitor, $\sigma$ may be readily approximated by averaging the absolute difference between the bandpassed and DC signals. This indication can then be evaluated for clinical purposes as a cardiac flow monitor (CFM) in a desired manner.

FIG. 7 illustrates a specific embodiment of the general system of FIG. 6, in which a true RMS value is obtained from only those AC components of the IR signal which lie within the frequency band most conducive to producing a meaningful flow signal. As shown in FIG. 7, the IR signal is first applied to a low-pass filter 46 which eliminates turbulence and electronic noise components of the IR signal above approximately 6 Hz.

The output of low-pass filter 46 is then applied to a high-pass filter 48 which rejects any frequencies below approximately 0.6 Hz to remove any artifacts due to very low frequency phenomena such as the patient's breathing. The output of the high-pass filter 48 is a narrow-band AC signal containing only frequency components lying between 0.6 Hz and 6 Hz. This narrowband signal is used as the input to a conventional RMS chip 50 whose output is the true RMS value (from a flow point of view) of the AC component of the IR signal.

Prior to being applied to the high-pass filter 48, the output of low-pass filter 46 is applied to a very-low-pass filter 52 which passes only frequencies below about 0.006 Hz—in other words, essentially only DC. The true RMS output of the RMS chip 50 (which corresponds to the standard deviation $\sigma$) is applied to the numerator of a divider 54. The output of the very-low-pass filter 52 (which constitutes the mean value $\mu$) is applied to the denominator of the divider 54. The output of the divider 54 is therefore the flow function $\sigma/\mu$.

The $\sigma/\mu$ flow function signal may be directly applied to the cardiac flow monitor for observation, or it may be integrated to produce an occlusion signal 55. This signal is suitable (when it is essentially zero) to alert medical personnel to a blockage of the blood flow across the distal end of the fiberoptic catheter, as for example because of a blood clot or a misplacement of the catheter against an artery wall.

The present invention has an additional advantage which is derived from the availability of the narrow-band signal 56 put out by the high-pass filter 48. Inasmuch as the narrow-band signal 56 essentially represents the true blood flow resulting from the patient's pulse, it can be clipped to a square wave shape by a clipper 58 and applied to a one-shot multi-vibrator 60 to provide a signal 62 representative of the patient's true pulse. This is significant for the following reason: referring again to FIG. 3, the heart action in a healthy patient is initiated by an electrical pulse within the body which can be sensed by electrocardiographic apparatus. In a sick patient, however, the EKG pulse may not propagate properly across the heart muscle, and the heart may either miss a pumping stroke or perform a spurious pumping stroke when no EKG pulse is present. By comparing the signal 62 to the EKG signal, these aberrations in the heart action can be readily observed.

By integrating the pulse signal 62, a true pulse rate signal 64 can be obtained for diagnostic purposes.

What is claimed:

1. The method of deriving blood flow information from a single color signal produced by a fiberoptic cardiac catheter, comprising the steps of:
   (a) filtering said signal to obtain its AC and DC components;
   (b) determining the RMS value of said AC component; and
   (c) dividing said RMS value by the value of said DC component.

2. The method of claim 1, in which said AC component has a wide frequency spectrum, said RMS value is a true RMS value representing the RMS value of only those frequencies of said AC component lying within a predetermined frequency band and said frequency band is selected to suppress those portions of said AC component which are generated by electronic noise, turbulence, and breathing.

3. The method of claim 2, in which said frequency band is on the order of 0.6 Hz to 6 Hz.

4. The method of claim 1, in which true pulse information is additionally derived from said signal by the further steps of:
   (d) clipping said AC component to produce a square wave signal; and
   (e) using said square wave signal to generate a signal representative of true pulse.

5. The method of claim 4, in which true pulse rate information is additionally obtained by the further step of integrating said true pulse signal.

6. The method of claim 1, in which said color signal is an infrared signal.

7. The method of claim 6, in which said infrared signal has a wavelength on the order of 820 nm.

8. Apparatus for determining blood flow from a single color signal in a fiberoptic cardiac catheter, comprising:
   (a) means adapted to provide a color signal input;
   (b) filter means adapted to receive said input to produce AC and DC signals representing, respectively, the AC and DC components of said color signal;
   (c) RMS-determining means connected to said filter means for determining the RMS value of said AC signal; and
   (d) divider means connected to said filter means and said RMS-determining means for producing an output representative of the RMS value of said AC signal divided by the value of said DC signal.

9. The apparatus of claim 8, in which said filter means include band-pass filter means for producing an AC signal containing only frequencies lying within a predetermined frequency band.

10. The apparatus of claim 9, in which said band-pass filter means includes means for limiting said frequency band to the range of 0.6 Hz to 6 Hz.

11. The apparatus of claim 9, in which said band-pass filter means include:
    (i) low-pass filter means for suppressing frequencies above the upper limit of said frequency band;
    (ii) high-pass filter means connected to said low-pass filter means for suppressing frequencies below the lower limit of said frequency band; and
    (iii) very-low-pass filter means connected to said low-pass filter means for suppressing essentially all frequencies other than DC;
    (iv) the output of said high-pass filter means being said AC signal, and the output of said very-low-pass filter means being said DC signal.

12. The apparatus of claim 11, further comprising:
    (e) clipper circuit means connected to said high-pass filter means for clipping said AC signal into a square wave; and
    (f) one-shot multivibrator means connected to said clipper circuit means for producing a pulse signal from said square wave.

13. The apparatus of claim 12, further comprising
    (g) integrating means connected to said multi-vibrator means for producing a pulse rate signal.

14. The apparatus of claim 12, further comprising
    (g) averaging means connected to said multi-vibrator means for producing a pulse rate signal.

15. The apparatus of claim 8, further comprising integrating means connected to said divider means for producing an occlusion signal.

* * * * *